(12) United States Patent
Hegedüs et al.

(10) Patent No.: US 9,625,478 B2
(45) Date of Patent: Apr. 18, 2017

(54) AUTOMATED INTEGRATED SLIDE-PROCESSING SYSTEM

(71) Applicant: 3DHISTECH KFT., Budapest (HU)

(72) Inventors: Márton Hegedüs, Budapest (HU); Béla Molnár, Budapest (HU); Tibor Virág, Budapest (HU)

(73) Assignee: 3DHISTECH KFT., Budapest (HU)

( * ) Notice: Subject to any disclaimer, the term of this patent is extended or adjusted under 35 U.S.C. 154(b) by 0 days.

(21) Appl. No.: 14/771,380

(22) PCT Filed: Feb. 28, 2014

(86) PCT No.: PCT/HU2014/000020
§ 371 (c)(1),
(2) Date: Aug. 28, 2015

(87) PCT Pub. No.: WO2014/132094
PCT Pub. Date: Sep. 4, 2014

(65) Prior Publication Data
US 2016/0011221 A1    Jan. 14, 2016

(30) Foreign Application Priority Data
Feb. 28, 2013   (HU) .................................... 1300124

(51) Int. Cl.
*A61B 10/00* (2006.01)
*G01N 35/00* (2006.01)
(Continued)

(52) U.S. Cl.
CPC ....... *G01N 35/00029* (2013.01); *G01N 1/312* (2013.01); *G01N 35/00584* (2013.01);
(Continued)

(58) Field of Classification Search
CPC .............................. B01L 1/00; G01N 35/1011
See application file for complete search history.

(56) References Cited

U.S. PATENT DOCUMENTS

| | | |
|---|---|---|
| 3,833,449 A | 9/1974 | Johnson |
| 4,428,793 A | 1/1984 | Sato et al. |
| | (Continued) | |

FOREIGN PATENT DOCUMENTS

| | | |
|---|---|---|
| AU | 2007254604 A1 | 1/2008 |
| EP | 1477838 A2 | 11/2004 |
| | (Continued) | |

OTHER PUBLICATIONS

PCT/HU2014/000020 International Preliminary Report on Patentability dated Jul. 27, 2015; 6 pages.
(Continued)

*Primary Examiner* — Jyoti Nagpaul
(74) *Attorney, Agent, or Firm* — Fitch, Even, Tabin & Flannery LLP (57) ABSTRACT

The present invention relates to an integrated automated slide processing system, especially to stain, to cover and to digitize one or more microscope slides (49) in one turn. Said system comprises, as a single apparatus, at least one incubation drawer, an incubation drawer carrier (1), a manipulation tray (2), a manipulation arm (3), a reagent changing unit (4), a washing and rinsing unit, a drop removal unit, a staining/pipetting unit (13), a coverslipping unit (14), a preview image recording unit (15), a digitizing unit (16) and a control computer (18) electrically connected with and providing control over said units, wherein each of the one or more unstained and un-covered microscope slides with sample to be stained, covered and digitized is arranged in an incubation drawer having sidewalls defining a vertically constrained slide receiving space, and wherein the above listed units form a treating path along which said microscope slide (49) is converted into a stained, covered and, at least partially, digitized microscope slide when simultaneously guided over said treating path upon and in harmony with (Continued)

respective control signals provided by the control computer (18) to the respective units.

18 Claims, 6 Drawing Sheets

(51) Int. Cl.
    *G01N 1/31*     (2006.01)
    *G01N 35/10*     (2006.01)
    *G01N 35/04*     (2006.01)

(52) U.S. Cl.
    CPC ..... *G01N 35/1002* (2013.01); *G01N 35/1011* (2013.01); *G01N 2035/00089* (2013.01); *G01N 2035/00138* (2013.01); *G01N 2035/00168* (2013.01); *G01N 2035/00356* (2013.01); *G01N 2035/0463* (2013.01)

(56) References Cited

U.S. PATENT DOCUMENTS

| | | |
|---|---|---|
| 4,985,206 A | 1/1991 | Bowman et al. |
| 5,418,138 A | 5/1995 | Miller et al. |
| 5,595,707 A | 1/1997 | Copeland et al. |
| 5,989,386 A | 11/1999 | Elliott |
| 6,076,583 A | 6/2000 | Edwards |
| 6,352,861 B1 | 3/2002 | Copeland et al. |
| 6,387,326 B1 | 5/2002 | Edwards et al. |
| 6,474,386 B2 | 11/2002 | Takahashi et al. |
| 6,495,106 B1 | 12/2002 | Kalra et al. |
| 6,568,447 B1 | 5/2003 | Sakai et al. |
| 6,673,620 B1 | 1/2004 | Loeffler et al. |
| 6,745,916 B2 | 6/2004 | Plank et al. |
| 6,796,353 B2 | 9/2004 | Lang et al. |
| 7,226,788 B2 | 6/2007 | De La Torre-Bueno |
| 7,270,785 B1 | 9/2007 | Lemme et al. |
| 7,368,081 B2 | 5/2008 | Thiem |
| 2003/0203493 A1 | 10/2003 | Lemme et al. |
| 2004/0002163 A1 | 1/2004 | Reinhardt et al. |
| 2004/0256963 A1* | 12/2004 | Affleck ............ C30B 7/00 312/209 |
| 2005/0186114 A1 | 8/2005 | Reinhardt et al. |
| 2006/0051253 A1 | 3/2006 | Gausepohl |
| 2006/0243199 A1 | 11/2006 | Kiene |
| 2007/0098599 A1 | 5/2007 | Thiem |
| 2007/0151672 A1 | 7/2007 | Takahashi et al. |
| 2014/0001337 A1* | 1/2014 | Corwin ............ G01N 1/312 250/208.1 |

FOREIGN PATENT DOCUMENTS

| | | |
|---|---|---|
| EP | 1890127 A2 | 2/2008 |
| EP | 2472265 A2 | 7/2012 |
| GB | 2441594 A | 3/2008 |
| WO | 9510035 A2 | 4/1995 |
| WO | 9721834 A1 | 6/1997 |
| WO | 9934190 A1 | 7/1999 |
| WO | 9949295 A1 | 9/1999 |
| WO | 03052386 A1 | 6/2003 |
| WO | 2004001389 A1 | 12/2003 |
| WO | 2005095575 A2 | 10/2005 |
| WO | 2006119585 A1 | 11/2006 |
| WO | 2007055366 A1 | 5/2007 |

OTHER PUBLICATIONS

PCT/HU2014/000020 International Search Report dated Oct. 28, 2014; 4 pages.

* cited by examiner

AUTOMATED INTEGRATED SLIDE-PROCESSING SYSTEM

CROSS-REFERENCE TO RELATED APPLICATIONS

This application is the National Stage of International Application No. PCT/HU2014/000020, filed Feb. 28, 2014, which claims priority to Hungarian Patent Application No. P1300124 filed Feb. 28, 2013.

The subject-matter of the present invention is an integrated slide processing system. In particular, the present invention relates to a combined automated apparatus for staining, covering and digitizing microscope slides, as well as to a process to be performed by such an apparatus in an automated manner, especially to stain, to cover and then finally to digitize microscope slides carrying biological samples.

Cell/tissue samples arranged on slides used in the pathological diagnostical work and in the field of biomedical research are not suitable for traditional optical microscopic study in their native state as they cannot provide images that are contrasty enough. Hence, there is a need to visualize, that is to stain certain cell/tissue structures. The most commonly used traditional staining processes (e.g. hematoxylin/eosin staining) merely allow a differentiation amongst the major cell components. By means of special reagents, specific detection and quantitative determination of certain molecules, as well as mapping of intracellular/intratissue distribution of said molecules in samples arranged on microscope slides become also possible. These techniques include inter alia immunohistochemical (IHC) and immunofluorescent (IF) processes which are based on antigene/antibody reactions and suitable for the specific demonstration of various antigenes, as well as Chromogenic or Fluorescent in-situ Hybridization (CISH, FISH) processes suitable for the specific demonstration of polynucleotides (for example DNS, RNS, mRNS, miRNS). To protect specimens and to improve the optical properties thereof, covering of the samples is required before a microscopic study of the stained samples is performed.

As far as practical implementation is concerned, a yet further important difference between traditional and molecule specific staining techniques is that in case of traditional staining processes, it does not matter if several samples are treated in the same staining solution which is often provided in larger amounts. The more sophisticated immuno or hybridization techniques, however, require the application of expensive reagents free of (cross-)contaminations in very small amounts; to this end, "disposable" reagents are preferred here. Besides manual techniques, this difference is equally present when automated section staining machines are considered. In certain traditional automated stainers, several slides are immersed into the dye-containing tanks of various design one after the other. Said stainers are clearly inappropriate to perform the modern specific staining processes which require more delicate techniques. To solve this problem, a great deal of patented solutions has become available.

Before/during applying staining, samples have to be pre-treated one after the other by several different reagents according to a given protocol and then stained. In the reaction steps performed with various reagents, it is a must to precisely set and then to maintain the incubation time and the incubation parameters (i.e. temperature, concentration) defined according to the protocol. The complex work process requires the employment of an assistant skilled at manual practice and has numerous possibilities to commit an error. A part of the reagents is hazardous to human health and/or to the environment. Hence, decreasing personal exposition and confining environmental loading by means of minimizing the amounts made use of are desirable. In this latter aspect, automation of the full process would result in obvious advantages. Moreover, the demand to perform diagnostical assaying in a standardized framework gets higher and higher in order that comparability of the measurements done at different times and on various samples in a given laboratory, as well as in various laboratories could be enhanced. Here, it plays the key role whether or not (pre-)treatment and evaluation of the samples take place in the same way, irrespective of time and location. For this reason, various automated section stainers have been developed recently.

International Publication Pamphlet No. WO03/052386 A1 and U.S. Pat. No. 6,495,106 B1 disclose apparatuses, wherein the slides are arranged horizontally side by side, and a manipulator head arranged on an arm moving above said slides along three spatial directions (X, Y, Z) drips the required reagent onto each of the slides after the reagent has been picked up by the head from one of the reagent containing vessels arranged beside the slides. The components required to rinse and dry said samples can also be found on the manipulator head itself.

International Publication Pamphlet No. WO95/10035 A1 discloses an apparatus of similar design, however, with such a basic difference that the manipulator head has to be changed automatically during the operation in order to perform each function. Slides occupy the same position during the entire staining process and all the required actions are carried out on the slides one after the other by the manipulator head which moves above the slides. Since the slides are located side by side, the apparatus needs a significant amount of space which is disadvantageous. A further disadvantage is that, due to the arm moving above a large surface area and carrying multiple manipulator heads, a large free volume portion remains above the tissue sections that facilitates non-desired drying of the samples during longer incubation times. A yet further problem is that a changeover between the slides and the reagents, as well as the completion of all the manipulations have to be performed by a single unit, that is the manipulator head, which leads to a limited throughput in time when several samples are to be handled. Moreover, it is apparent to a skilled person in the art that the application of reagents on the microscope slide surfaces simply in drops does not ensure in most cases the even coverage of the entire sample at all.

According to U.S. Published Patent Application No. 2003/0203493, as well as U.S. Pat. No. 7,270,785 B1 and U.S. Pat. No. 6,352,861 B1, the microscope slides are arranged in a carousel slide support. Slides are brought into position under units which are arranged in fixed positions and manipulate the slides by rotating the slide support. Here, instead of pipetting, reagents are applied on the sample by means of direct dispensing from separate reagent containing vessels arranged side by side in a second rotating carousel support which locates above said carousel support with microscope slides. An even spreading of the reagents is provided by the oily cover layer and the nozzle-aided mixing known from U.S. Pat. Nos. 5,418,138 and 5,595,707. To bring the appropriate reagent onto the proper microscope slide, motions of both the slides and the reagents are required in technical solutions with carousel supports. Besides the large outer dimensions of this kind of solutions, another disadvantage appears in that only the entire carousel support can be filled up with slides and/or emptied all at once: after an apparatus of this type has been put in action, it can no longer, i.e. afterwards, accept further microscope slides and, in turn, samples that have already been stained cannot be removed until all samples become stained. Therefore, the work process halts before the evaluation and/or the additional digitization of the samples; assuming about forty to fifty tissue sections and treating times of several hours this results in a rather significant loss of time.

Cover component of U.S. Pat. No. 4,985,206, as well as cover components taught in U.S. Published Patent Application No. 2006/0051253 A1 and International Publication Pamphlet No. WO2004/001389 A1 help with achieving an even distribution of reagents over the sample and hindering evaporation via exploiting the capillary effect. In case of applying this latter solution in automated machines, dispensing of reagents onto microscope slides arranged side by side in drawers takes place by pipetting which is performed in such a way that liquid is dispensed from a pipette tip moving in three directions (X,Y,Z) at the vicinity of the end portion of said covering component, and said liquid then soaks into between the covering component and the microscope slide surface. In a machine of this type, samples are arranged in drawers containing ten to twelve microscope slides each; said drawers can be replaced in operation.

According to the teaching of International Publication Pamphlet No. WO2005/095575 A2 and U.S. Pat. No. 6,673,620 B1, liquids used to fill up incubation chambers formed by rubber gasket sealings below and above the individual microscope slides are transported through a pipe system. In case of consecutive dispensing of different reagents, the risk of mixing-up of the reagents and/or a significant loss of reagents occur along the pipe sections in common.

Besides autostainers, separate automated machines to accomplish the task of tissue section coverslipping have also been developed. Most of these machines impose a glass coverslip onto the specimen after applying cover substance thereon, similarly to histological technique performed manually. Without providing a complete list of references, various patented techniques are known from e.g. U.S. Pat. No. 4,428,793; and EP Patent No. 1,477,838 B1; as well as U.S. Pat. Nos. 5,989,386; 3,833,449; 6,474,386 B2; 6,568,447 B1 and 6,796,353 B2; and furthermore from U.S. Published Patent Application No. 2006/0243199 A1 and Australian Published Patent Appl. No. 2007254604 A1. Moreover, U.S. Published Patent Application No. 2007/0151672 A1 teaches technical details of dispensing a rolled-up cover tape.

Some of the apparatuses also capable of covering the tissue sections besides the staining thereof are constructed by combining a separate stainer and a separate coverslipper arranged side by side, wherein to transfer tissue sections, an output opening of said stainer faces to an input opening of the coverslipper and wherein means for tissue section transferring are also provided. An apparatus designed in this way is known e.g. from U.S. Published Patent Application No. 2007/0098599 A1 and U.S. Pat. Nos. 6,745,916 B2; 7,368,081 B2; as well as from International Publication Pamphlet No. WO2007/055366 A1. Furthermore, U.S. Pat. Nos. 6,076,583 A1; 6,387,326 B1; as well as EP Patent No. 1,890,127 A2 and U.S. Published Patent Application No. 2004/0002163 A1 disclose such devices, wherein the mentioned two functions are combined integrally.

In particular, U.S. Published Patent Application No. 2005/0186114 A1 discloses a combined automated coverslipping and staining apparatus that also comprises an optical reading unit, preferably a bar code reader, to ease identification of samples (that is, microscope slides) treated by the apparatus itself.

Numerous patents are issued on digital microscopes working separately from automated staining and coverslipping devices which are suitable for digitizing the already stained and coverslipped biological samples. The digital microscopes available today can only receive ready samples.

After completing the staining of the given slides and before proceeding with the work process, depending on the type of the automated staining apparatus, completion of other slides have to be waited for. After this, the samples are transported together for coverslipping and then to microscopic examination/digitization. The work process requires permanent surveillance of a biopsy assistant since connecting separate pieces of equipment and the reposition of samples are performed manually. To date, the staining, coverslipping and digitization steps of the work process have been served by several different devices, which requires excessive space and costs. Slides are put on wait again and again until their treatment, one after the other, takes place. Accordingly, each unit will be left idle for a longer period of time without utilization, then processing of several slides becomes necessary at the same time, and for this reason, different devices performing their given functions become point of congestion time and again during the work process. Such limited throughput causes the extension of the work process. In case of forty to fifty tissue sections and several hours of treatment times this results in a considerable extent of time loss. Thus, based on the previous notion, the integration of staining/coverslipping containing steps which can be partly performed in parallel and the subsequent processing and image analysis by means of microscopes with processing the slides on a one-by-one basis into a single apparatus did not seem reasonable from the aspect of time utilization. However, the time loss accumulated during the multiple-stage work process can cause delays in diagnosing and applying the appropriate therapy; moreover, in cases of certain samples degrading over time, it can even cause a decay in sample quality (e.g. fading of fluorescent chromogens, occurrence of artifacts due to coverslipping, sample aging and external contaminations). To date, no such prior art combined devices have been known that are suitable for optimizing the time usage of said work process and thus also resolving the above-mentioned problems, and would be capable of fully automated staining, coverslipping, digitization and/or evaluation of samples.

EP Patent No. 2,472,265 discloses an automated system for processing biological samples which comprises an automatic transport module for transporting microscope slides with biological sample between workstations, a stainer module, a coverslipper module, a module for recording a pre-view image, a digitizing module, a storage module, as well as a computer directly controlling said module for transporting the slides. The above listed units are basically connected to each other linearly, in series, wherein each microscope slide will pass along said workstations formed as different subunits.

U.S. Pat. No. 7,226,788 discusses an automated stainer which determines one or more regions of a given microscope slide where samples can be found and which are thus to be stained by taking a preliminary image of the slide and via recording and processing of a low resolution pre-view image of said slide. When staining takes place, based on the recorded pre-view image and after localizing the sample, the automated machine first contours the biological sample (or specific parts thereof) with a hydrophobic marking substance. Then, said machine carries out the actual staining of the thus marked regions by pumping reagents through tubes of small cross-section into the region(s). In certain cases contouring the samples can be rather complicated and it is also a notable aspect that to accomplish it, an additional substance and respective mean(s) of delivery are also required beyond the reagents.

It is well-known that the optical imaging device—generally provided in the form of a microscope—which carries out the digitization of microscope slides with sample is very sensitive to contamination because of the optics applied therein. Therefore, when connecting (integrating) coverslipper and stainer modules with such kind of an optical imaging device, in particular a digital microscope, it is a highly considerable problem to avoid contaminating the optical device (and, in given cases, the optics thereof) by slides passed from the relatively contaminated coverslipper and stainer modules to the optical device.

The object of the present invention is to eliminate the above mentioned problems and to work out a solution which enables the staining, coverslipping and digitization of slides to be performed simply and in an automated manner, while optimized duration of the time period required to perform said subprocesses is also ensured, without contaminating the applied digitization unit.

The intended object of the invention has been achieved by providing an automated integrated slide processing system according to claim 1. Preferred embodiments of said system in the form of various pieces of equipment are set forth in claims 2 to 8.

The invention is further explained in detail with reference to the attached drawing along with preferred non-limiting embodiments, wherein.

As can be seen in FIGS. 1 to 8, the above aim has been resolved by a complex and compact automated slide processing system according to the invention that equally comprises staining, coverslipping and (preferably high resolution) digitizing units, wherein said slide processing system comprises incubation drawers, an incubation drawer carrier, a manipulation tray, a manipulation arm, a reagent changing unit, a washing and rinsing unit, a drop remover air blade, a preview image recording unit, as well as a computer controlling the above mentioned subunits/modules, wherein one or more unstained and uncovered microscope slides with sample is/are arranged in at least one, in a preferred embodiment preferably in ten to two hundreds incubation drawers designed to be positioned beside and above one another through manual or automatic feeding; here, sidewalls of said incubation drawers converge in direction Z and said incubation drawers are disposed in an incubation drawer carrier equipped with appropriate insertion sensors.

With such design of the incubation drawers, the space required for storage can be minimized. This allows for the device to have a compact size and to occupy the least lateral space possible; it also allows a precise inspection and control of the environmental parameters that are critical from the aspects of staining and biological reactions. The sidewalls convergent along direction Z of the drawers of the apparatus that receive various microscope slides ensure that liquids dispensed onto a slide surface could not run off. Even if the bottom of the microscope slide contacts the sidewall, due to the obliquity of said sidewall, the top surface of the slide will not be in contact with the sidewall, and therefore the liquid spreading over the top surface will stay in its position.

Also, the above mentioned design of the incubation drawers enables relatively free, multiple movements of the slides between various parts of the staining and coverslipping unit and the digital microscope, and therefore said design also ensures the integrability of the staining, coverslipping and digitizing subprocesses while avoiding contaminating the applied digitizing unit, which in certain cases, can be a digital microscope as well.

Figure 5:
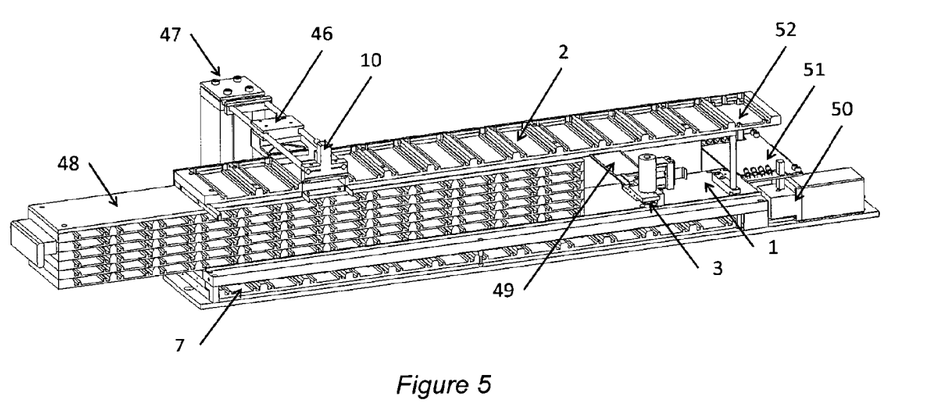
FIG. 5 illustrates the manipulation tray, the sample holder of the preview unit, the manipulation arm, the incubation drawer unit, the washing and rinsing unit and the drop remover air-blade constituting subunits of the preferred embodiment depicted in FIGS. 1 and 2 in the state where the outer casing of the apparatus is removed.

The manipulation arm 3 is affixed to a rail arranged in parallel with the incubation drawer; by means of a belt drive, it performs movements parallel to the longitudinal axis (direction Y) of the microscope slides 49 and movements perpendicular to that direction (direction X). A motor located on the manipulation arm 3 moves a slide gripping arm mounted at the end of the manipulation arm along the Z direction by means of a belt drive.

The slide gripping arm includes a sensor and a gripping mechanism. The latter—in its preferred embodiment—consists of a blade and a respective clip, wherein said clip is moved by an electromagnet. The sensor detects whether the incubation drawer is empty or it contains a slide 49. To protect the slides and to achieve better adhesion, the clip can be rubber-coated. When moved, the microscope slide 49 is inserted into between the blade and the clip. The manipulation arm 3 carrying out X- and Y-direction movements by means of a motor and a belt drive controlled by a control computer 18 is capable of moving said slides 49 with the blade of the slide gripping arm performing movements in direction Z by means of a motor and a belt drive and the clip operated by an electromagnet between the incubation drawers as well as to or from the manipulation tray 2, to or from the preview unit 15, to or from the washing and rinsing unit 7 formed under the incubation drawer carrier 1, to or from a drop remover unit installed in at least one cell of the manipulation tray 2, to or from the coverslipping unit 14, to or from the staining/pipetting unit 13, to or from digitizing unit 16 and onto or from said feeding tray.

In case of a preferred embodiment of the invention, the manipulation tray 2, which is installed parallel to the incubation drawer and placed above it, is provided by a tray of at least two cells open from above, wherein the cells are placed side by side in a linear manner, and wherein at least one cell of the tray, that locates below the preview image recording unit 15, is open from below as well. Moreover, at least one of the cells of said tray contains a drop remover air-blade unit 10. Sidewalls of each cell of said manipulation tray 2 converge in direction Z.

Figure 3:
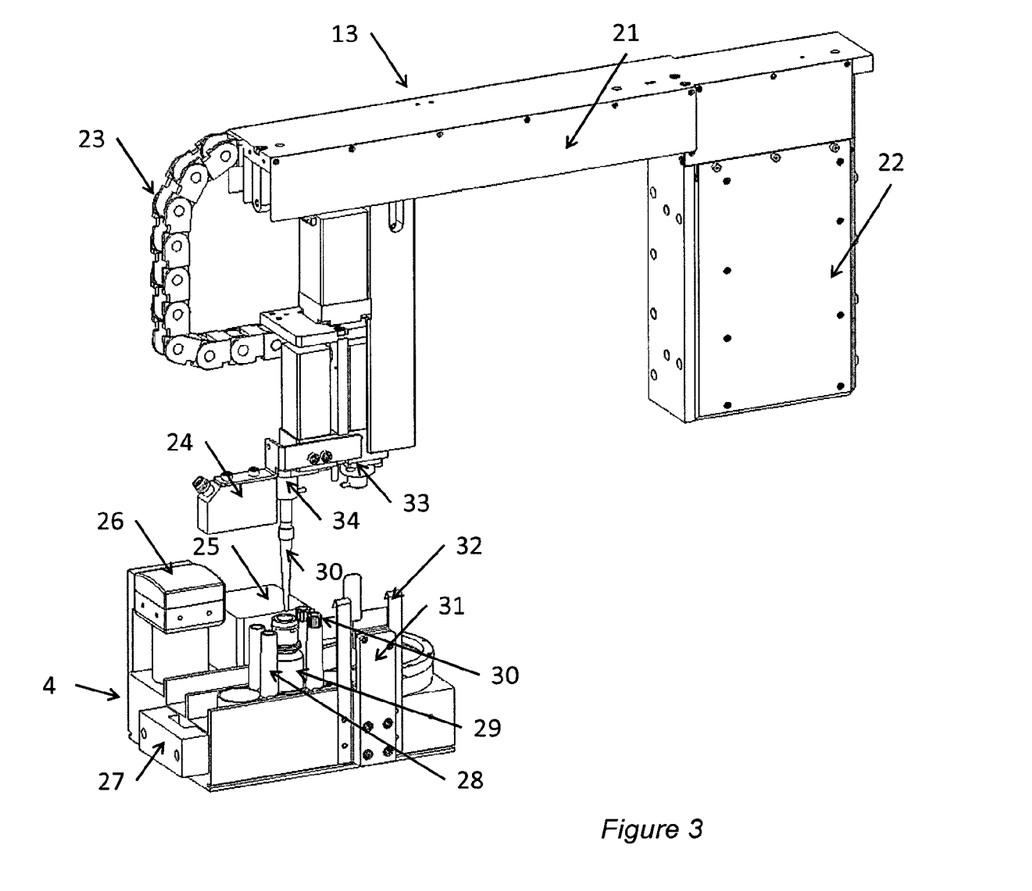
FIG. 3 shows the exemplary staining/pipetting and reagent changing unit of the preferred embodiment illustrated in FIGS. 1 and 2 separately.

The assembly according to the invention contains a staining/pipetting unit 13 constructed to be located above the manipulation tray 2, said staining/pipetting unit comprises a pipette tip pickup head 34 able to move in three spatial directions by means of stepping motors, a spindle and a gear-armed actuation mechanism and connected via a pipe system to a piston 33, which is connected the control computer 18, as well as a liquid level sensor 24. One or more energy chain(s) 23 establish connections between the module control electronics 22 attached to a top support 21 and some moving parts.

The apparatus according to the invention contains at least one preview unit installed above one of the cells 52 of the manipulation tray 2 also open from below; such unit comprises a camera and/or code reader unit, a respective optics and an illumination system 51 which are connected to the control computer 18. Illumination system 51 has a special design: it illuminates the complete surface area of the slide 49 from the bottom, obliquely at an angle less than 90 degrees in such a way that only light scattered from the surface of the tissue sample can reach the camera. Direct light beams of the light source form angles with the optical axis of the camera and applying a proper masking, they take no role in imaging. Thus a dark background is formed. Light beams that get scattered in the field of view will change their direction and can reach the objective of the camera. Such beams thus show up the location of scatter centres (e.g. tissue sample) in front of the dark background.

The apparatus according to the invention also contains at least one reagent changing unit 4 which comprises a video camera and/or code reader unit connected to the control computer 18, a stepping motor also connected to said computer 18, as well as a train of vessel holding chain links connected to the stepping motor. Here, the vessel holding chain links used to store different reagents are provided at their edges with a control element facilitating connection, preferably with knobs and recesses; furthermore, at least one pipette tip holder 41 is formed on each chain link, wherein a separate own pipette tip 30 belongs to each reagent. In this way, the occurrence of cross-contamination among the reagents can be eliminated. Moreover, the presence of pipette tips and reagent vessels is detected by a sensor 31. The length of the chain of reagents can be varied according to the number of reagent vessels 29 and/or reagent chain links 28 to be applied. Forwarding and moving of the chain of small vessels is carried out by a stepping motor 25 in such a way that at the time of stepping the vessels from one position into another, the camera 26 and/or code reader unit takes a digital image of an identifier located at the bottom of the vessels and said image is then processed by the control computer 18 and/or decoded by a code reader unit. The chain of reagents is located on a specifically constructed covered reagent tray 5 which allows to store the chain of reagents in refrigerators and, at the same time, the direct placement of the chain of reagents within the apparatus on a special supporting element 27 suitable for this purpose.

Figure 6:
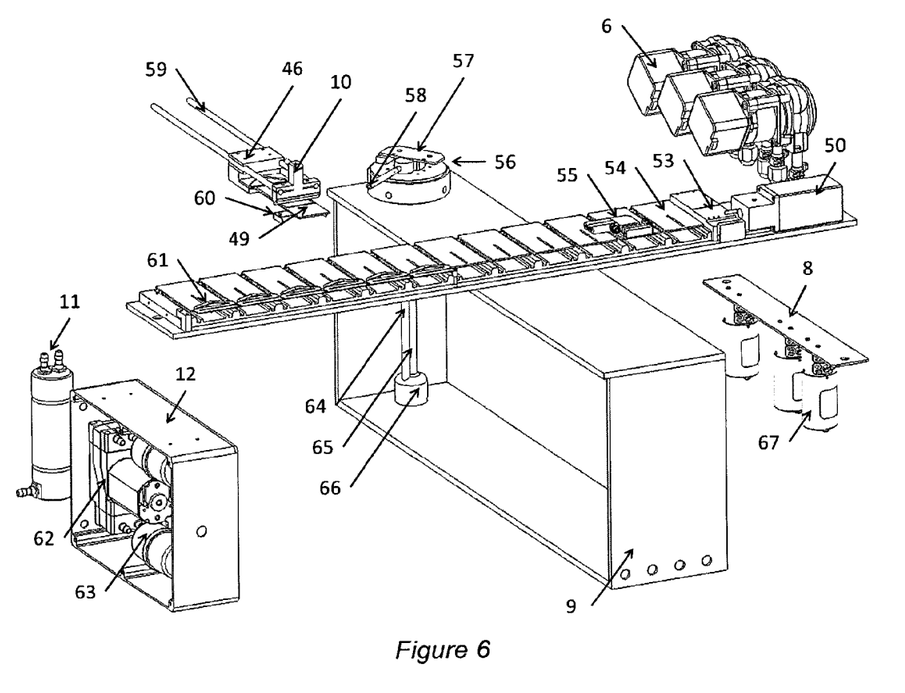
FIG. 6 presents further details of the washing and rinsing unit and the drop remover unit of the preferred embodiment shown in FIGS. 1 and 2.
Figure 7:
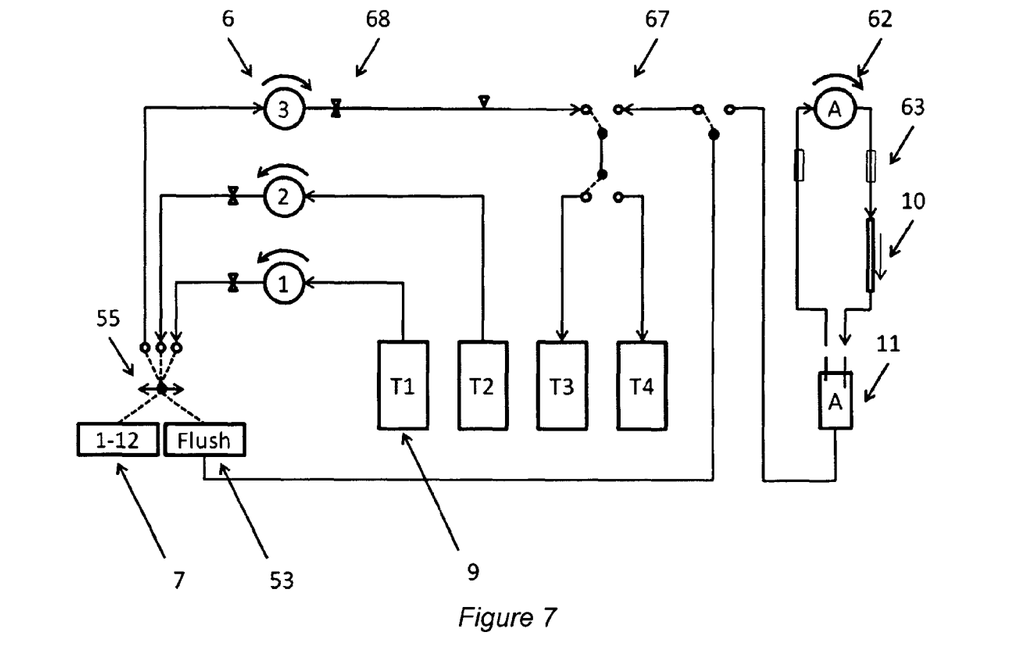
FIG. 7 depicts schematically the fluid and pneumatic system of the preferred embodiment of the automated combined staining-coverslipping-digitizing apparatus according to the invention.

The apparatus according to the invention contains at least one washing and rinsing unit which is formed in one of the preferred embodiments under the incubation drawer carrier 1 and comprises at least one, preferably two or more washing and rinsing cells 7 that have conical-shape top 54 with an opening located at the peak of the cone. The conical-shaped washer top design enables the control and even flooding of the complete surface of slides 49, as well as the almost total removal of liquid through the same opening by utilizing the surface tension of liquids. In parallel with the top of washing and rinsing cell 7, at least one slider 55 can move on a rail, said slider 55 is connected by a pipe to pumps 6; the sliders are provided with at least one, preferably three openings. Said openings of the sliders, depending on the position of the slider driven by a motor 50, are either aligned with the openings on the top surfaces of cells, the venting holes and the opening of the docking position 53 or they are closed. The slider moving among the cells and provided with several openings can substitute a large number of electromechanical valves. This solution has the advantage that the length of the common pipe sections required for accessing each washing and rinsing cell and, consequently, the chance of cross-contamination between liquids are minimal. Springs are placed on the rail mounted parallel to the incubation drawer carrier 1 in order to hold the slide 49 in position during filling and emptying of the cells. In this way it can be avoided that the force generated by the surface tension of liquids would cause the movement of slides within the cell. Washing and rinsing unit 6 contains at least one washing liquid tank, at least one storage tank for spent washing liquid, and a sensor with a bell-shaped cover 66 for measuring liquid levels within each tank, as well as respective sensors for identifying the tanks. In a preferred embodiment, the tanks 9 can be removed and the fluid connection 64 and the liquid level measurement 65 (through a sensor electronics 57 required for this) take place via cap 56 of the tank equipped with a bayonet-joint. To ensure proper mobility for the cap within the device, said cap 56 is connected to the frame structure by a so-called mobile "umbilical cord" containing pipe 58 and lines. The system can include a valve terminal 8 comprising one or more valve(s) 67, which allows venting and dewatering of the pipe system, as well as separation of the hazardous and non-hazardous waste. The pipe system can also contain safeguards against overpressure and/or service access at one or several points 68.

The apparatus according to the invention comprises at least one drop removing unit located in at least one of the cells of the manipulation tray 2; this drop removing unit comprises a supporting column 47, supporting rods 59, an air blade 10, a sucking tray 46, slide adjusting lugs 60, a drop-removing unit 11 in the form of a drop-catcher dish, a compressor unit 62 and a silencer 63, a pipe system connecting fluidically these elements and a sound insulation casing 12. Said drop removing unit comprises high and low pressure parts connected with one another in a semi-closed system; the parts connected in series can operate simultaneously. The quick operation and the special design of said drop removing unit allows the removal of liquid films while avoiding undesired drying of the tissue samples. The drop removing unit keeps liquids strictly within its own components thus avoiding the contamination of the other units or the samples.

Figure 4:
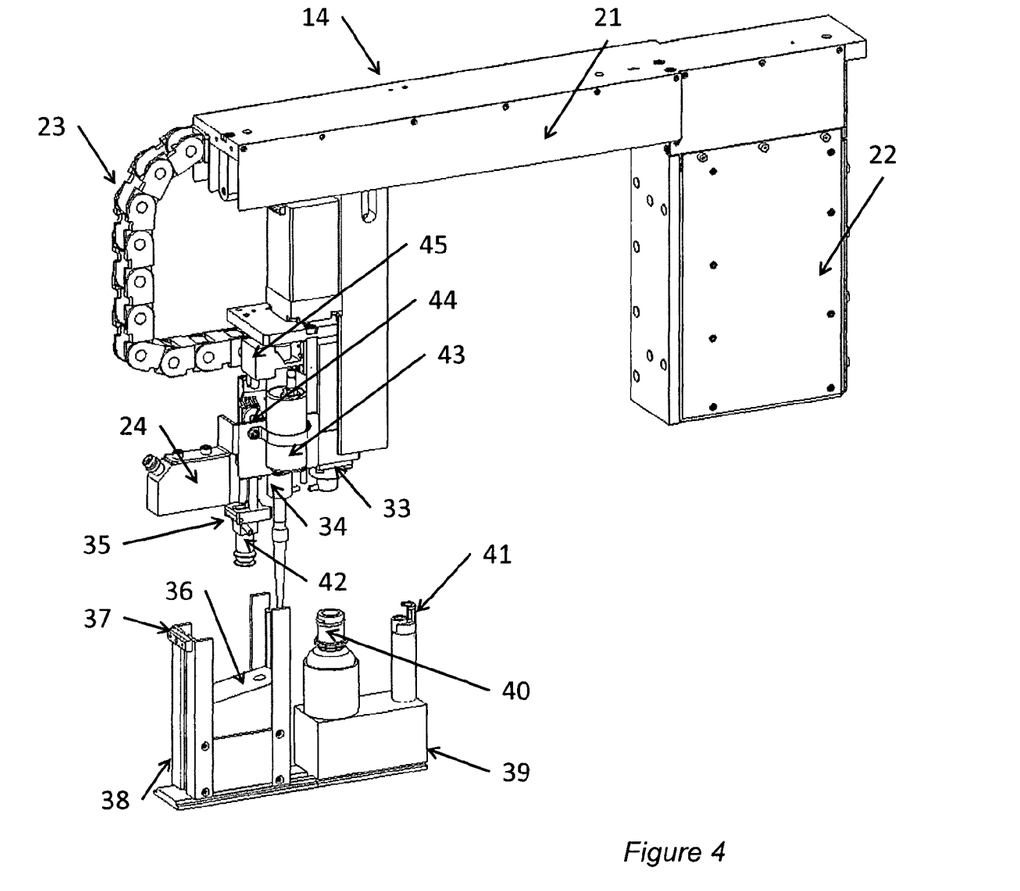
FIG. 4 shows the coverslipping unit and the storage unit for the consumable covering substance of the preferred embodiment illustrated in FIGS. 1 and 2.

The apparatus according to the invention comprises at least one coverslipping unit 14. One or more energy chains 23 establish connection between module control electronics 22 fixed to a top support 21 and some of the moving parts. The coverslipping unit comprises a manipulator part, which is able to move in two spatial directions, as well as a piston 33, a vacuum system, a covering substance tank 39, a liquid level sensor 24, a pipette tip holder 41, a pipette tip sensor and a storage unit 38 for coverslips; here the manipulator part comprises a pipette tip pickup head 34, coverslip pickup means 42 and an electronic unit electrically connected to the control computer 18 controlling them; wherein the vacuum system comprises a pump 45, a silencer 43, a pressure sensor 44, a vacuum valve and a sucking disc, wherein an opening is established on the top of the covering substance tank for transferring covering substance into the pipette and wherein the internal structure of the coverslip storage unit is such that surface 36 on which coverslips are laid forms an angle with the horizontal plane and wherein the tilting angle of the sucking disc for the coverslip 42 can be changed by a customized special compact mechanic structure 35 in such a way that during a vertical movement of the coverslip pickup means 42, only the tilting angle of said coverslip changes without the movement of the lower edge thereof.

Figure 1:
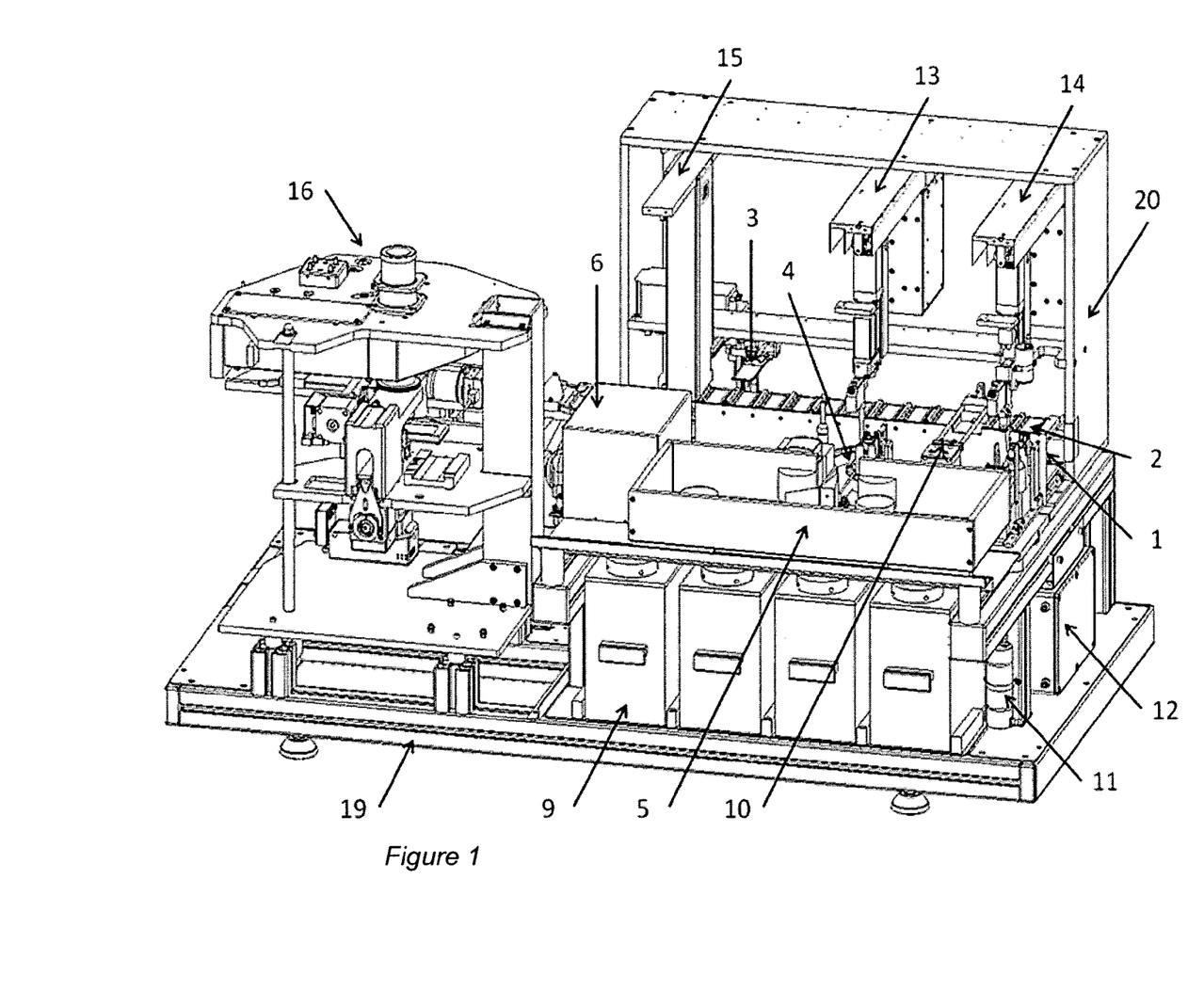
FIG. 1 is a front elevational view of a preferred embodiment of the automated combined staining-coverslipping-digitizing apparatus according to the invention.
Figure 2:
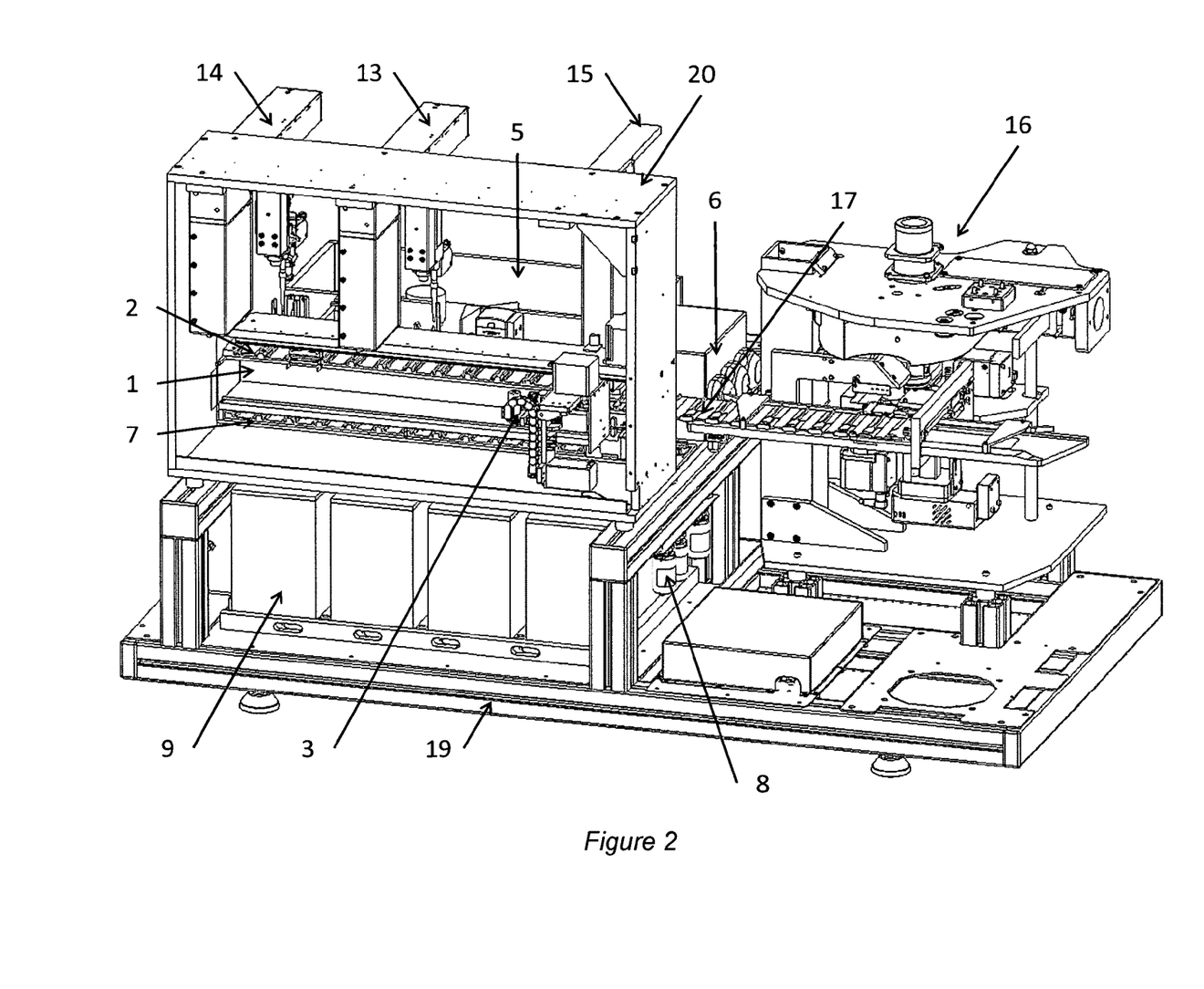
FIG. 2 is a rear view of the embodiment presented schematically in FIG. 1.

The apparatus according to invention comprises a digital microscope or digital slide scanner, which is located on base frame structure 19 next to the staining/covering frame structure 20. Digitizing unit 16 consists of a feeding tray for receiving slides 49, a tray moving mechanism and a digitizing unit 16 wherein the feeding tray 17 is installed parallel to the manipulation tray 2, wherein the tray moving mechanism and the digitizing unit 16 are connected to the control computer 18.

Figure 8:
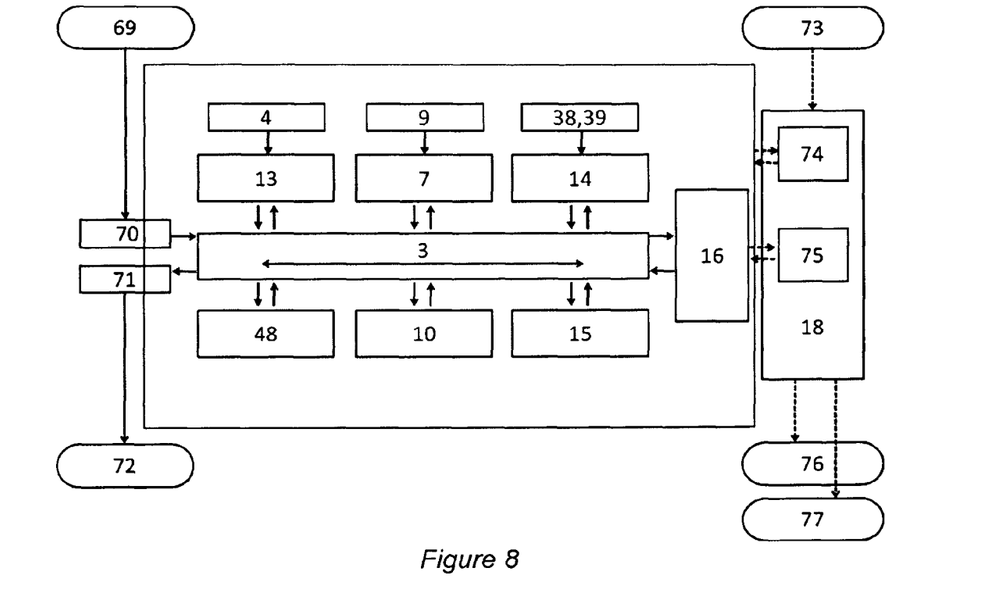
FIG. 8 illustrates schematically the operation principle of the automated staining-coverslipping-digitizing apparatus according to the invention.

According to the invention, the incubation steps typically taking longer durations of time within the staining-covering-digitizing and evaluation work process will be performed in parallel, with several slides processed at the same time. The implementation of manipulation steps taking shorter time but requiring higher technical level is serial from the aspect that each slide 49 will be inserted one after another into one or more task-specific units. However, in other respects, the performance of manipulation steps can also be considered as parallelized since different manipulation units (e.g. staining/pipetting, covering, washing and rinsing, drop removing and digitizing units) can work on different slides at the same time independently from one another.

Task-specific units can work on different samples parallel to each other. In addition, a great advantage of the integrated system is that the modules are designed in such a way that they maximally complement each other with respect to tasks to be performed on each sample. This way such a work process becomes available, which requires complex accordance and which cannot be implemented within other systems, and which allows the precise treatment of samples and considerable saving of the extent of reagent. This process requires the matching of the operation of the preview image recording, pipetting, loading, incubation, washing and rinsing and drop removing units as well as the well-fitting design of affected modules highly adaptable to complex work processes. A kind of preview image on which tissue sample can be localized and mapped can only be acquired from unstained and uncovered samples only by specially custom-designed illumination. The tool path will then be prepared by means of the map thus received; along this path, the precise pipetting unit can perform the feeding of reagent in reality. The staining unit feeds reagent to the tissue by moving the pipette tip along such a path that will move over the complete surface of the tissue with the given incrementation and thus it allows even spreading of the reagent over the entire surface of the sample. In this way only such amount of reagent is required, that is actually needed for the given sample and, therefore, it can be avoided that the reagents cover unnecessary slide areas. During pipetting, a difference between wetting of a hydrophilic tissue sample and a slide with hydrophobic surface, as well as the surface tension will inhibit the uncontrolled spreading and flowing of reagent liquids. In order to keep reagents on the tissue surface, the loading parameters (e.g. accelerations) and the modul design (e.g. sidewalls of drawers converging in direction Z) should be constructed in such a way that liquid could not flow off the tissue. The loading, the incubation and the washing/rinsing drawers, as well as the washing and rinsing and drop removing units are designed in such a way that liquid could not get to the bottom or side of the slide (from where other parts of the apparatus could be contaminated). Before subsequent pipetting, the liquid film formed after washing needs to be removed by means of the drop remover, otherwise the reagent can spread and get diluted on the wet surface. The coordinated and precise operation of different units discussed above makes unnecessary a process—applied in certain other solutions—which is related to the contouring of tissue samples by a hydrophobic marker. The modules which are designed with taking into account the surface tension of liquids and various wetting of different surfaces ensure considerable savings on the extent of reagents. This way not only cost saving can be achieved with respect to reagents which can be rather expensive in some cases but the load of hazardous materials on workers and the environment can also be reduced. During the coordinated multistep pipetting/washing and rinsing/drop removing process, the efficiency of removing different reagents from the sample is rather high, and, accordingly, a lower extent of cross-contaminations and a high grade of staining can be expected in comparison to other methods.

To operate the apparatus according to the present invention, the incubation drawer 48 will be filled manually or via a slide feeding unit 70 with unstained, uncovered and labeled slides 69; then the incubation drawer 48 will be placed into the incubation drawer carrier 1; then one needs to fill/load the washing tanks with washing liquid, the chain links of the reagent changing unit with reagent containing vessels, the pipette tip holders 41 of the chain links with pipette tips 30, the covering substance tank 40 with covering substance and the coverslip storage unit 38 with coverslips; the already used pipette tips 30 and the tanks full of spent material will have to be removed from the system.

the slide 49 is gripped by the motor driven manipulation arm 3 by holding it between the blade of the slide gripping arm mounted on a rail and the rubber coated clip; then said arm moves the slide 49 from the incubation drawer along a certain path in directions X-Y-Z; then the arm moves the slide 49 by means of a belt drive in directions X-Y-Z into the cell opened from below located under the preview unit of the manipulation tray 2, where the illumination system illuminates said slide 49 at an angle of incidence lower than 90 degrees; thus light scattered from the sample to be stained will reach the camera of the preview unit. The image created this way is recorded by control computer 18. Since the device records an image of the entire surface of the slide 49, a second light source located above the slide 49 is switched on, and thus the label area of said slide 49 will also be recorded and thus the slide 49 can be identified in this way. Not all samples appear on traditional preview images of digital microscopes in proper contrast. In such cases, the optimization of digitization can be assisted by better quality photos of unstained and uncovered tissues taken with special illumination means. Based on the thus created digitization map, the staining procedure can also be optimized. A staining for a given slide 49 can be ordered through the control computer 18. After recording preview images of each slide 49, the control software 79 calculates an optimal staining of said slides 49 while taking into consideration different incubation times of different staining protocols 73, the dimensions of each tissue to be stained and other factors.

Control computer 18 calculates the path to be run by the pipette tip 30 during each staining, taking also into account the shape of the tissue to be stained. In this way, only a part of the tissue will be stained, not the whole slide 49, therefore the usage of reagent decreases considerably. In cases of certain samples (e.g. fluorescent staining technique), contrast of the preview image recorded from an unstained and uncovered sample can also be used for optimizing the digitalization. The preview image, the staining of tissue samples and the digitization can be further optimized based on data which can be acquired from a common database related to the sample (e.g. in knowledge of the distribution and location of TMA cores).

At the time of starting the staining, the slide 49 is transferred into a cell of manipulating tray 2 by manipulation arm 3. The pipette tip pickup head 34 of the staining//pipetting unit 13 located above the manipulation tray 2 moves above the reagent chain of changeable length reagent changer by means of a stepping motor. Simultaneously, the reagent changing unit ensures the setting of reagent chain containing small vessels of reagents 29 into proper position. Then the pipetting head, moving in direction Z, is connected to the pipette tip holder and then, together with the pipette, it moves downwards. After this, the driving motor of the staining//pipetting unit 13 transfers a pipette tip 30 into a vessel containing the given reagent; then, by means of the piston, it sucks up staining substance in the amount requested to stain the tissue area on the given slide. By means of the motors, staining/pipetting unit 13 moves the pipette tip containing stain above the unstained slide 49 located in a given cell of the manipulation tray 2 and following a path calculated previously by the control computer 18, it transfers stain onto the tissue by means of the piston and ensures the even spreading of the given reagent by moving the pipette tip 30. the pipette tip 30 is then returned to the respective reagent chain link 28 by the pipette tip remover part 28. Furthermore, the pipetting unit is also capable of preparing dilutions and reagent mixtures which can take place in dedicated vessels or even on the surface of the slide 49 or the tissue sample. the stained slide 49 is placed into an incubation drawer by the manipulation arm 3 for a duration according to the staining protocol 73. The sidewalls of the incubation drawer converge in direction Z to avoid that the reagent run off the slide 49. Due to the small air volume in the incubation drawers, drying time of the sample increases. When the incubation time has run out, the stained slide 49 is moved by the manipulation arm 3 to the washing and rinsing cell of the washing and rinsing unit. The top of the washing and rinsing cell 7 and the cell constitute a closed system. The opening of the slider matches the opening designed at the top of the washing and rinsing cell 7 and the pump attached to the slider sucks up material from the washing material tank and then transfers into the cell through its top opening. The top has a conical design, therefore it distributes liquid evenly within the cell. The entered washing material will be removed by a pump from the cell after a period of incubation time set out by the staining protocol and then the pump will transfer it into the used washing substance tank. The separation of hazardous and non-hazardous waste is made possible through the proper adjustment of the valve terminal 8 of the washing and rinsing unit 6. During pumping out the washing substance, the capillary force generated in the cell would lift the slide 49 upwards which is prevented by springs 61 attached to the rail for fixing the slide in position. After washing and rinsing, the slide 49 will move to a new staining phase or it is transferred to a drop removal unit located in at least one cell of the manipulating tray 2 by means of the manipulation arm 3. At the time of inserting the slide 49, the sucking tray 46 is pushed backward and the compressor switches on and pumps air in a way that an air-blade is created in an angle with the slide 49; simultaneously with pulling out the slide 49, sucking tray 46 will push forward through a spring connection continuously contacting the edge of the slide. The air blade blows all over the slide 49 and any liquid in excess will tumble over the edge of the slide 49 and is sucked up by the compressor through bores formed at the edge of the sucking tray. The liquid will be separated from the air circulated by the compressor of the drop removing unit 11 within the drop removing unit 11 which is also in fluid communication with the washing and rinsing unit.

After drop removal, the slide 49 will be transferred either into staining phase or to coverslipping unit 14. The manipulator head will be moved by a stepping motor to a position above the pipette tip holder 41 belonging to the respective covering substance, picks up the pipette tip by means of the pipette tip pickup head 34, then moves to a position above the covering substance tank and puts the pipette into the covering substance, sucks up covering substance by means of the piston and then moves to a position above the slide 49 and transfers the covering substance onto the slide 49 by means of the piston 33. Then the manipulator head puts down the pipette tip and moves to a position above the coverslip storage unit 38; the control computer 18 switches on the pump, the sucking disc contacts the surface of the coverslip and the vacuum sucks said coverslip to the sucking disc. Considering that the internal arrangement of coverslip storage unit 38 enables the bending of coverslips by means of cam 37 located there after the clamping of coverslips, this bending facilitates the separation of stuck coverslips and eventually, only one single coverslip will be lifted by the manipulator head. Then manipulator head moves to a position above slide 49. Initially, the coverslip is at an angle with the horizontal plane, but the mechanical design of said manipulator head ensures that during the placement of the coverslip, it will gradually get to a position parallel to slide 49. In the meantime, due to specifically designed joint mechanism, the coverslip will no longer move into a direction parallel to the plane of sample which ensures a careful handling of the tissue. At the same time, the number of bubbles trapped in the covering substance between the slide 49 and the coverslip can be minimized. Subsequently, by eliminating the vacuum, the coverslip will be released. Then the microscope slide 49 will be transferred into an incubation drawer or into a position of the feeding tray of the digitization unit 16 by means of the manipulation arm 3.

A slide 49 located on the feeding tray will be transferred to the digitizing unit 16 by means of the slide moving mechanism, where the preparation of a digital slide 76 can be performed from stained and covered tissue sample 72. Since the image recorded by the preview image recording unit determines the appropriate location of the digitization and the size of the area to be digitized, the digitizing unit 16, possibly comprising (in given cases) a subunit of a digital microscope or even a complete digital microscope, will record only the area in question and thus it shortens the time required for digitalization. The preview image used to optimize the digitization can be provided by the digitizing unit 16, but a photo taken of an unstained and uncovered sample at the beginning of the process or a combination the two possibilities can equally be used. The special illumination technique developed for unstained and uncovered samples ensures proper contrast even in cases of samples which contain no or hardly any visible stain. In cases of weakly stainable samples, the preview image taken of unstained and uncovered samples, recorded in the course of the contrast enhancement process can be better for use and may then have higher contrast than the preview image recorded later on by the digitizing unit 16, which does not include contrast enhancement. For this reason, in cases of certain samples, to optimize the digitization, it might be useful to exploit the preview image recorded in the unstained and uncovered state of the sample. The exact course of digitization is disclosed in another document, and various versions thereof are known to a person skilled in the art. The digital slide 76 can be subjected to image analyzing algorithms 75.

After digitization, slide 49 will be transferred to the dispensing unit 71 or into the incubation drawer from where it can be dispensed or removed by the operating staff.

Manipulation steps will be performed by partly independent manipulation units. This modular arrangement facilitates the assembly of the device, the repair of eventual malfunctions, and the replacement of parts, if required.

Because of their independency, the time requirements for manipulation steps are not related to the moving unit. Different manipulating steps can be carried out simultaneously regarding several slides 49 while moving an additional slide 49 which, in the case of 41 to 50 sections and several hours of treatment time, may result in considerable time saving. Because of the complex arrangement of slides 49 to be treated, the length of required movements and their respective time demand can also be reduced. Further time-saving can be achieved by the fact that the feeding and removal of slides 49 can also be performed one by one, even by digitizing unit 16 or by means of (a) special unit(s). The staining of samples can be carried out with different kind of reagents based according to staining protocols 73 with different lengths. For this reason, it is a great advantage that samples the staining of which is finished earliest can proceed to further steps of the work process: covering, then digitizing and evaluation without having to wait for the other samples. In the case of integrated devices, permanent surveillance provided by a biopsy assistant is not required for monitoring and waiting for all the samples to be finished. Besides the acceleration of the work activities, the archiving of ordinary samples and samples degradable in time can also be solved. Through the fine tuning of complementary modules, a kind of complex work process can be accomplished within an integrated system, which is not possible in other systems and by which considerable saving of reagent can be achieved. Furthermore, in the present complex process, a decreased extent of exposure of workers and the environment to hazardous substances and that of cross-contaminations causing staining artifacts.

Furthermore, by moving the slides 49 one by one between the modules, it can be accomplished that the manipulator units operating in serial mode (i.e. on one slide at a time), which otherwise presents a very limited throughput, could operate with the best utilization of time possible. At the time of completing a given process, slide 49 can be removed by the robotic arm and the next specimen can be placed in the module. This way, the staining, covering, digitizing and evaluation units can work simultaneously: up to even all units can be processed in certain phases of the work process at the same time in such a way that there would always be an appropriate extent of time available for the completion of the current task. All these make it possible that the specimens can be treated simultaneously according to several staining protocols by the present integrated apparatus even in cases of continuous operation. Also, insertion of samples arrived late and/or requested to be processed urgently shall not be a problem. Accordingly, the first results 77 which can be obtained through carrying out the analyses of samples will become available as early as possible.

The invention claimed is:

1. An integrated automated slide processing apparatus to process, especially to stain, cover and digitize, one or more microscope slides (49) with bottom and top surfaces, said top surface carrying a biological sample, the apparatus comprising at least one incubation drawer (48), an incubation drawer carrier (1), a manipulation tray (2), a manipulation arm (3), a reagent changing unit (4), a washing and rinsing unit, a drop removal unit, a staining/pipetting unit (13), a coverslipping unit (14), a preview image recording unit (15), a digitizing unit (16) and a control computer (18) electrically connected with and providing control over said units, wherein
 the at least one incubation drawer comprises converging sidewalls defining a slide receiving space, said converging sidewalls are obliquely arranged such that even when the bottom of the microscope slide contacts the sidewall, the top surface of the microscope slide and said sidewall are apart from one another, and
 the above listed subunits together form a treating path within the apparatus, said treating path being configured to convert each of said microscope slides (49) into stained, covered and, at least partially, digitized microscope slides when the slides are guided over said treating path upon and in harmony with respective control signals provided by the control computer (18) to the respective subunits.

2. The automated slide processing apparatus of claim 1, wherein a manipulation tray (2) is arranged operatively connected to the staining/pipetting unit (13), said staining/pipetting unit (13) is displaceable in three spatial directions by stepping motors, a spindle and a gear-armed actuation mechanism and includes a pipette tip pickup head (34) and a liquid level sensor, said pipette tip pickup head (34) being connected via a pipe system with a piston connected to the control computer (18).

3. The automated slide processing apparatus of claim 1, wherein the manipulation tray (2) comprises at least one slide receiving cell being equally open on its top and bottom, and wherein the preview image recording unit (15) is positioned to face said slide receiving cell so as to acquire a preview image of an unstained and uncovered sample on a microscope slide located in said slide receiving cell to create a digitization map of the slide.

4. The automated slide processing apparatus according to claim 3, wherein the preview image recording unit (15) comprises a camera and/or code reader unit electrically connected to the control computer (18), a respective optics, and an illumination system for illuminating the microscope slide (49) under acute angles.

5. The automated slide processing apparatus of claim 3, wherein the digitization map of the microscope slide (40) created by the preview image recording unit (15) is constructed to optimize both staining and digitization of said slide when the slide is guided over the treating path.

6. The automated slide processing apparatus of claim 1, wherein the manipulation tray (2) further comprises at least one cell adapted to receive the drop removal unit.

7. The automated slide processing apparatus of claim 6, wherein the drop removal unit comprises an air-blade, a suction tray, a compressor unit and a pipe system establishing a fluid communication of said elements.

8. The automated slide processing apparatus of claim 6, wherein the drop removal unit further comprises a silencer and a sound insulation casing.

9. The automated slide processing apparatus of claim 1, wherein the coverslipping unit (14) includes a manipulator unit adapted to be displaced in two spatial directions, a piston, a vacuum system, a mounting medium tank, a liquid level sensor, a pipette tip holder, a pipette tip sensor and a coverslip storage unit, wherein
the manipulator unit comprises a pipette tip pickup head, a coverslip pickup means, an electronics for controlling said elements and connected electrically to the control computer (18);
the vacuum system comprises a pump, a pressure sensor, a vacuum valve, and a coverslip pickup suction cup;
an opening is formed in the top of the mounting medium tank to provide mounting medium in the pipette,
wherein said coverslip storage unit is provided with an internal structure in which a surface supporting the coverslips forms an angle with the horizontal plane and the tilting angle of the coverslip pickup suction cup is adapted to be varied by a customized compact mechanism in such a way that when the coverslip pickup means moves vertically, only the tilting angle of the coverslip changes without its lower edge being displaced.

10. An integrated automated slide processing apparatus to process, especially to stain, cover and digitize, in one turn and one by one, one or more microscope slides (49) with bottom and top surfaces, said top surface carrying a biological sample, the apparatus comprising at least one incubation drawer (48), an incubation drawer carrier (1), a manipulation tray (2), a manipulation arm (3), a reagent changing unit (4), a washing and rinsing unit, a drop removal unit, a staining/pipetting unit (13), a coverslipping unit (14), a preview image recording unit (15), a digitizing unit (16) and a control computer (18) electrically connected with and providing control over said units, wherein
each of the at least one incubation drawer is configured to receive one of the one or more unstained and uncovered microscope slides with sample to be stained, covered and digitized for multiple movements of said slides within the apparatus;
the incubation drawer carrier (1) is configured to receive said at least one incubation drawer;
the manipulation tray (2) is configured to receive said microscope slides (49) from the at least one incubation drawer to perform at least partial processing of the slides;
a manipulation tray (2) is arranged operatively connected to the staining/pipetting unit (13);
the preview image recording unit (15) is configured to acquire a preview image of the unstained and uncovered sample on the slide to create a digitization map of said slide; and wherein
individual ones of the at least one incubation drawer are constructed with converging sidewalls defining a slide receiving space, said converging sidewalls obliquely arranged such that even when the bottom of the microscope slide contacts the sidewall, the top surface of the microscope slide and said sidewall are apart from one another, and
the above listed subunits together form a treating path within the apparatus, said treating path being configured to convert each of said microscope slides (49) into stained, covered and, at least partially, digitized microscope slides when the slides are guided over said treating path upon and in harmony with respective control signals provided by the control computer (18) to the respective subunits.

11. The automated slide processing apparatus of claim 10, wherein the staining/pipetting unit (13) is displaceable in three spatial directions by stepping motors, a spindle and a gear-armed actuation mechanism and includes a pipette tip pickup head (34) and a liquid level sensor, said pipette tip pickup head (34) being connected via a pipe system with a piston connected to the control computer (18).

12. The automated slide processing apparatus of claim 10, wherein the manipulation tray (2) comprises at least one slide receiving cell being equally open on its top and bottom, and wherein the preview image recording unit (15) is positioned to face said slide receiving cell.

13. The automated slide processing apparatus of claim 12, wherein the preview image recording unit (15) comprises a camera and/or code reader unit electrically connected to the control computer (18), a respective optics, and an illumination system for illuminating the microscope slide (49) under acute angles.

14. The automated slide processing apparatus of claim 10, wherein the digitization map of the microscope slide (49) created by the preview image recording unit (15) is constructed to optimize both staining and digitization of said slide when the slide is guided over the treating path.

15. The automated slide processing apparatus of claim 10, wherein the manipulation tray (2) further comprises at least one cell adapted to receive the drop removal unit.

16. The automated slide processing apparatus of claim 15, wherein the drop removal unit comprises an air-blade, a suction tray, a compressor unit and a pipe system establishing a fluid communication of said elements.

17. The automated slide processing apparatus of claim 15, wherein the drop removal unit further comprises a silencer and a sound insulation casing.

18. The automated slide processing apparatus of claim 10, wherein the coverslipping unit (14) includes a manipulator unit adapted to be displaced in two spatial directions, a piston, a vacuum system, a mounting medium tank, a liquid level sensor, a pipette tip holder, a pipette tip sensor and a coverslip storage unit, wherein
the manipulator unit comprises a pipette tip pickup head, a coverslip pickup means, an electronics for controlling said elements and connected electrically to the control computer (18);
the vacuum system comprises a pump, a pressure sensor, a vacuum valve, and a coverslip pickup suction cup;
an opening is formed in the top of the mounting medium tank to provide mounting medium in the pipette,
wherein said coverslip storage unit is provided with an internal structure in which a surface supporting the coverslips forms an angle with the horizontal plane and the tilting angle of the coverslip pickup suction cup is adapted to be varied by a customized compact mechanism in such a way that when the coverslip pickup means moves vertically, only the tilting angle of the coverslip changes without its lower edge being displaced.

* * * * *